United States Patent [19]

Pierce et al.

[11] Patent Number: 4,490,147
[45] Date of Patent: Dec. 25, 1984

[54] ABSORBENT SANITARY NAPKIN

[76] Inventors: Larry L. Pierce; June S. Pierce, both of 4120 Vansant Rd., Douglasville, Ga. 30135

[21] Appl. No.: 399,303

[22] Filed: Jul. 19, 1982

Related U.S. Application Data

[63] Continuation-in-part of Ser. No. 213,233, Dec. 5, 1980, Pat. No. 4,340,058.

[51] Int. Cl.³ ............................................. A61F 13/16
[52] U.S. Cl. ................................................... 604/378
[58] Field of Search ............... 604/378, 385, 372, 387, 604/358, 370

[56] References Cited

U.S. PATENT DOCUMENTS

| 3,344,789 | 10/1967 | Arnold et al. | 604/378 X |
| 3,369,544 | 2/1968 | Cockford | 604/385 X |
| 3,371,667 | 3/1968 | Morse | 604/378 X |
| 4,072,150 | 2/1978 | Glassman | 604/378 X |
| 4,240,416 | 12/1980 | Boich | 604/378 |

Primary Examiner—John D. Yasko
Attorney, Agent, or Firm—Thomas & Kennedy

[57] ABSTRACT

The sanitary napkin includes a base layer 21 of absorbent sheet material, an elongated dry, swellable sponge 27 extending along and supported by the base layer of sheet material, and a cover layer 22 of absorbent sheet material joined at its edge portions to the edge portions of the base layer and covering the sponge. Elongate pads 24, 25 and 26 are arranged parallel to one another and held in a bundle with the sponge 27 by the base layer and cover layer of sheet material.

16 Claims, 20 Drawing Figures

U.S. Patent  Dec. 25, 1984  Sheet 1 of 3  4,490,147
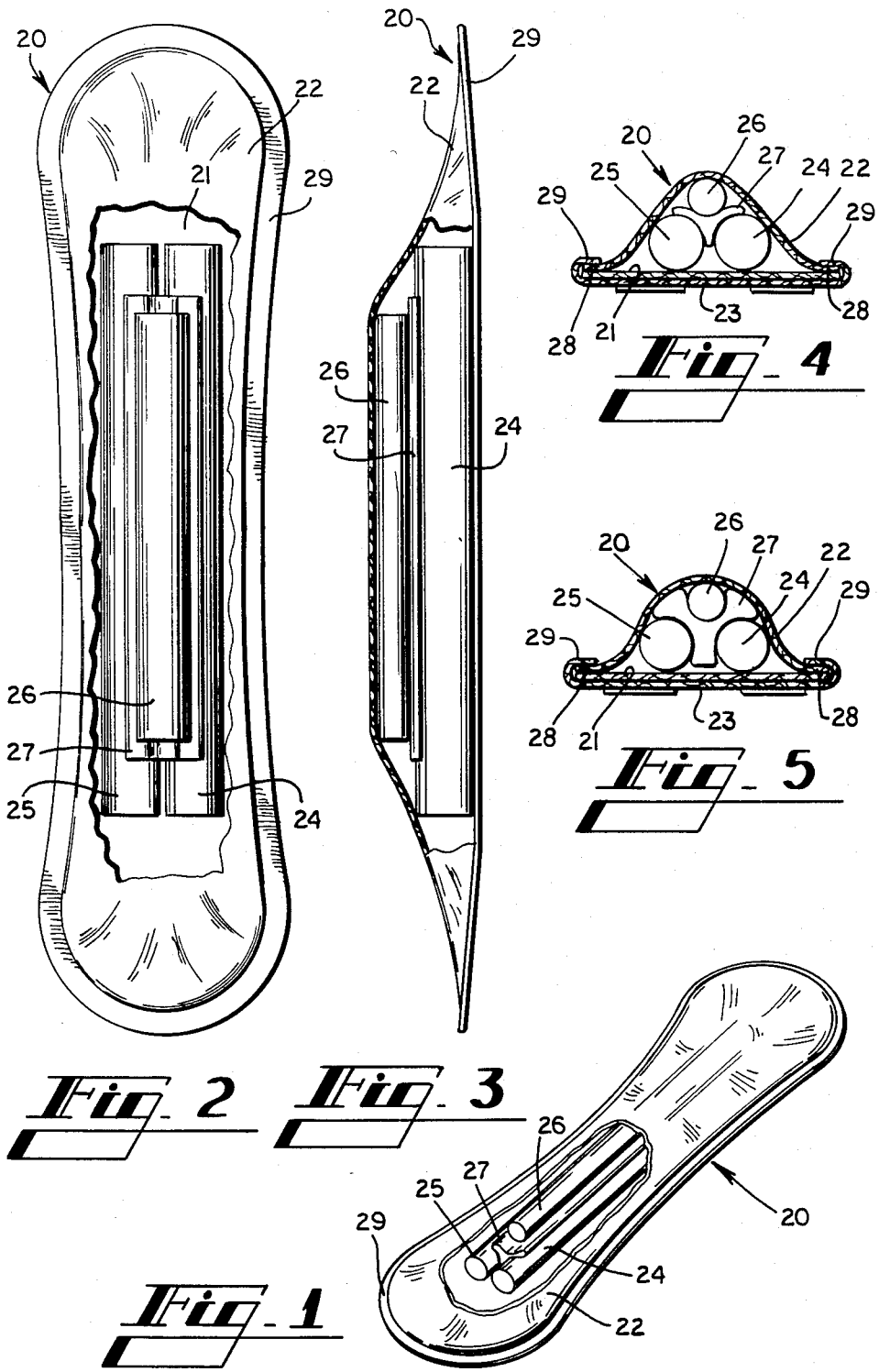

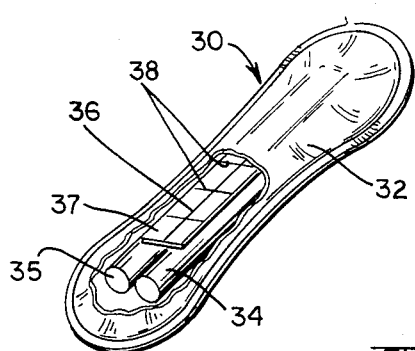
Fig_6
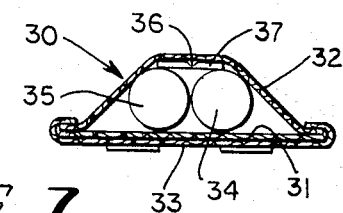
Fig_7
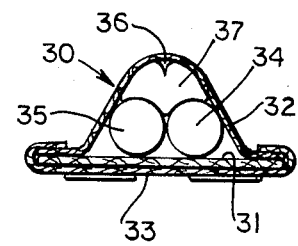
Fig_8
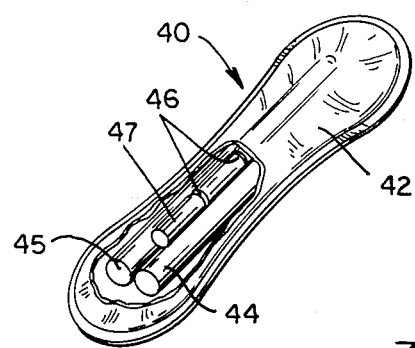
Fig_9
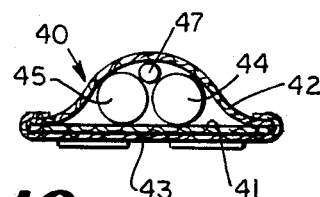
Fig_10
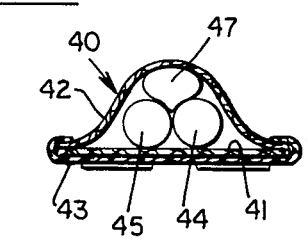
Fig_11
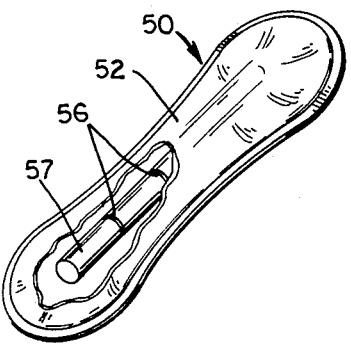
Fig_12
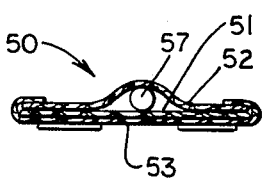
Fig_13
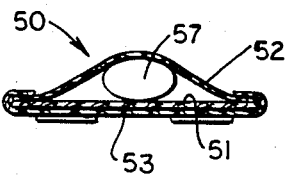
Fig_14

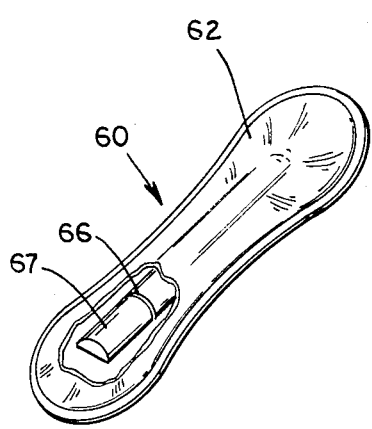
*Fig_15*
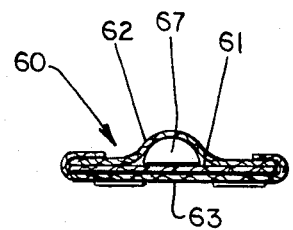
*Fig_16*
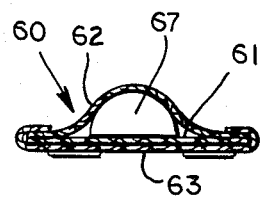
*Fig_17*
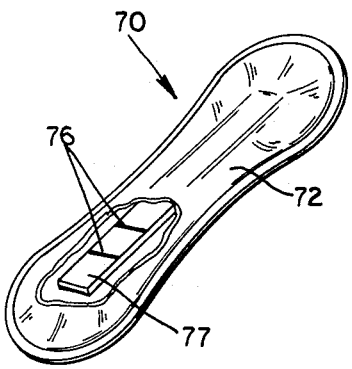
*Fig_18*
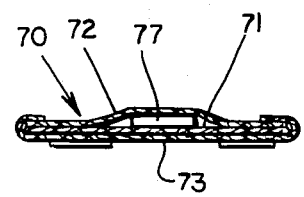
*Fig_19*
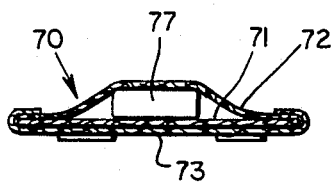
*Fig_20*

ABSORBENT SANITARY NAPKIN

CROSS REFERENCE TO RELATED FILE

This is a continuation-in-part of U.S. patent application Ser. No. 213,233 filed Dec. 5, 1980, now U.S. Pat. No. 4,340,058, issued July 20, 1982.

BACKGROUND

This invention relates to a sanitary napkin which is formed from liquid-absorbent material and is worn for collection of menstrual fluids. More particularly, the sanitary napkin includes at least one elongated swellable sponge supported on a base layer of absorbent sheet material, and a cover layer of absorbent sheet material joined at its edge portions to the edge portions of said base layer of sheet material and extending about and covering the sponge. Optionally, additional elongate pads extend parallel to and adjacent to said sponge.

Sanitary napkins or pads which are worn externally by women for the collection of menstrual fluids must be of sufficient absorbency in order to function to collect fluids, but in order to increase the absorbency of prior art napkins, the napkins usually have been increased in bulk, either in thickness or in width, or both, in order to provide additional material for absorbing the liquids. The thick or wide napkins usually are uncomfortable to the wearer, and when the thick napkins are compressed during normal use by the wearer, the material of the napkin is less capable of absorbing and retaining the fluids. Additionally, sanitary napkins sometimes tend to become twisted or shifted out of proper position when in use, causing discomfort to the wearer and reducing the ability of the napkin to collect the fluids.

Various stiffeners, belts and adhesive strips have been used in the past in order to help sanitary napkins to retain their shape and to keep their position during use, but these features have not been completely effective in solving the above-listed problems.

In general, it is desirable to the wearer of a sanitary napkin to have the napkin of small width and thickness and of a shape that fits comfortably in the space available and yet have the napkin capable of absorbing and retaining a large amount of menstrual fluids.

SUMMARY OF THE INVENTION

Briefly described, the present invention comprises a sanitary napkin which is to be worn for the collection of menstrual fluids, and which comprises a base layer of absorbent sheet material, an elongate dry, swellable sponge extending along and supported by the base layer of sheet material, additional elongate pads extending parallel to and adjacent the sponge, and a cover layer of absorbent sheet material joined at its edges to the edges of the base layer of sheet material and covering over the sponge and pads. The sponge is a bio-compatible, polymeric, elastomeric, lint-free and uniformly swellable sponge and is characterized by an absorption capacity for liquids in excess of twenty times the weight of the sponge. The sponge also is characterized by having been compressed during its production, and it is placed between the base and cover layers of the absorbent sheet material in a dried condition. The sponge is very thin when compressed and still in its dried condition, and when menstrual fluids are passed to the napkin and contact the sponge, the sponge swells upon absorbing the menstrual fluids, growing in thickness.

The elongate sponge is located centrally of the length of the absorbent sheets of material of the napkin, and the sponge is scored across its length so as to enhance its bendability along its length, thereby permitting the napkin to conform to the natural curvature of the body of the wearer, and the protrusion formed in the napkin by the sponge is alignable with the labia of the wearer so that the sponge is properly positioned to receive menstrual fluids upon their emission from the body.

In some embodiments of the invention, the sponge is combined with other elongate pads arrange in a bundle within the layers of absorbent sheet material of the napkin, and the sponge and the pads are loosely contained within the bundle and are movable relative to one another, both longitudinally and laterally, so that the napkin can be bent along its length and conform to the shape of the anatomy. The sponge and the pads are arranged in a triangular configuration with the sponge locted at or near the top of the triangle where it is most likely to be contacted by the menstrual fluids from the wearer, and the pads support the sponge and provide more absorbable material adjacent the sponge to increase the capacity of the napkin to absorb liquid.

In other embodiments of the invention the sponge is used in the napkin without any elongate pads.

The elongate sponge material can be of varied cross-sectional shapes as may be desired by the producer, and when the sponge expands in response to absorbing menstrual fluids, the sponge becomes extremely soft and tends to fill the spaces within the layers of absorbent sheet material of the napkin and to conform to the shape of the body of the wearer.

Thus, it is an object of this invention to provide a sanitary napkin for use in the collection of menstrual fluids, which is comfortable to the wearer, and which is capable of absorbing a large volume of menstrual fluid, and which is capable of being shaped to the anatomy of the wearer during use.

Another object of this invention is to provide a sanitary napkin that comprises at least one elongated, swellable sponge located between a base sheet and a cover sheet of absorbent material, with the sponge being swellable when contacted by menstrual fluids.

Another object of this invention is to provide a sanitary napkin which is relatively thin prior to use but which has the ability to absorb a relatively large amount of liquid and which grows in thickness upon absorption of liquid.

Other objects, features and advantages of the present invention will become apparent upon reading the following specification, when taken in conjunction with the accompanying drawings.

BRIEF DESCRIPTION OF THE DRAWINGS

FIG. 1 is a perspective illustration of the sanitary napkin, with a portion of the cover layer of absorbent sheet material being removed to expose the pads and sponge.

FIG. 2 is a plan view of the napkin of FIG. 1, with a portion of the cover layer removed to expose the pads and sponge.

FIG. 3 is a side view of the napkin of FIG. 1, with a portion of the cover layer of the sheet material removed to expose the pads and sponge.

FIG. 4 is an end cross-sectional view of the napkin of FIG. 1, showing the sponge material before it has been contacted by menstrual fluids.

FIG. 5 is a cross-sectional view of the napkin of FIG. 1, similar to FIG. 4, but showing the sponge in its swollen condition after having absorbed menstrual fluids.

FIG. 6 is a perspective illustration of the sanitary napkin, similar to FIG. 1, but showing a second embodiment of the invention.

FIG. 7 is an end cross-sectional view of the napkin of FIG. 6.

FIG. 8 is an end cross-sectional view of the napkin of FIG. 6, but showing the sponge in its swollen condition after having been contacted by menstrual fluids.

FIG. 9 is a perspective illustration of the sanitary napkin, similar to FIGS. 1 and 6, but showing a third embodiment of the invention.

FIG. 10 is an end cross-sectional view of the napkin of FIG. 9.

FIG. 11 is an end cross-sectional view of the napkin of FIG. 9, similar to FIG. 10, but showing the sponge after it has swollen from contact with menstrual fluids.

FIG. 12 is a perspective illustration of the sanitary napkin, similar to FIGS. 1, 6 and 9, but showing a fourth embodiment of the invention.

FIG. 13 is an end cross-sectional view of the napkin of FIG. 12.

FIG. 14 is an end cross-sectional view of the napkin of FIG. 12, similar to FIG. 13, but showing the sponge material after it has become swollen from contacting menstrual fluid.

FIG. 15 is a perspective illustration of the sanitary napkin, similar to FIGS. 1, 6, 9 and 12, but showing a fifth embodiment of the invention.

FIG. 16 is an end cross-sectional view of the napkin of FIG. 15.

FIG. 17 is an end cross-sectional view of the napkin of FIG. 15, but showing the sponge material in its swollen condition after having contacted menstrual fluids.

FIG. 18 is a perspective illustration of the sanitary napkin, similar to FIGS. 1, 6, 9, 12 and 15, but showing a sixth embodiment of the invention.

FIG. 19 is an end cross-sectional view of the napkin of FIG. 18.

FIG. 20 is an end cross-sectional view of the napkin of FIG. 18, similar to FIG. 19, but showing the sponge material after it has been swollen from contact with menstrual fluid.

DETAILED DESCRIPTION

Referring now in more detail to the drawings, in which like numerals indicate like parts throughout the several views, FIGS. 1-5 illustrate a sanitary napkin 20, which comprises a base layer 21 of absorbent sheet material, a cover layer 22 of the same material, a substantially impervious wrapping layer 23, elongate absorbent pads 24, 25 and 26, and an elongate pad 27 of sponge material. The cover layer 22 is joined at its edge portion 28 to the edge of the base layer 21 about the entire perimeter of the base layer, and the wrapping layer 23 is turned upwardly at its edge portion 29 and attached to the upper surface of the edge portion 28 of the cover layer 22. The connection between the cover layer, base layer and wrapping layer is by an adhesive.

The elongate absorbent pads 24, 25 and 26 are arranged parallel to one another, with pads 24 and 25 arranged in side-by-side relationship to form a base layer of pads, and with pad 26 arranged parallel to pads 24 and 25 but positioned over the adjacent surfaces of pads 24 and 25 in a triangular relationship. Pad 26 is shorter than pads 24 and 25 so that their ends are staggered or offset from each other. The elongate sponge 27 is a bio-compatible, polymeric, elastomeric, lint-free, uniformly swellable hydrophilic sponge which has been compressed to a low profile (FIGS. 3 and 4), and preferably would be less than one-eight inch thick in its dried condition, and would be expandable to about four times its thickness. For example, the sponge material can be of the type described in U.S. Pat. No. 4,098,728, issued July 4, 1978. The sponge can be die-cut and compressed, or extruded. Other sponge materials can be utilized, but it is highly desirable that the sponge material be compressed, of a low profile, and swellable upon contact with menstrual fluid or other liquids so as to wick the liquid and hold the liquid, at least temporarily, adjacent the pads of the napkin. It is also desirable that the sponge material have an absorption capacity for liquids in excess of twenty times the weight of the sponge.

As illustrated in FIGS. 4 and 5, the sponge 27 is of low profile, and is nestled in a bundled relationship between the pads 24, 25 and 26, so that it contacts all three pads. When the sponge 27 is contacted by menstrual fluids, the sponge tends to expand to those spaces available between the pads 24, 25 and 26, and within the base and cover layers of the absorbent sheet material 21 and 22. The sponge becomes extremely soft upon swelling and tends to be confined between the pads 24, 25 and 26, as illustrated in FIG. 5, and the interface between the sponge 27 and the pads 24, 25 and 26 tends to cause the sponge to absorb the menstrual fluid that is not already absorbed by the pads, and after the menstrual fluid has been absorbed by the sponge 27, and if the sponge should be compressed by the wearer, the menstrual fluids absorbed by the sponge 27 will tend to move along the length of the sponge, and in some cases, move to the surface of the sponge where the fluids will contact the pads 24, 25 and 26 and become absorbed by the pads. In addition, the relatively liquid-impervious wrapping layer 23 tends to prohibit the movement of the menstrual liquid from the pads and sponge, thereby containing the liquids within the napkin.

The base layer 21 and cover layer 22 of the napkin are formed of absorbent sheet materials such as pulp fiber with a thin overlayer of spun polypropylene, while the relatively liquid-impervious wrapping layer 23 is formed of polyethylene. The pads 24, 25 and 26 can be formed of pulp fiber with overlayers of spun polypropylene.

A second embodiment of the invention is disclosed in FIGS. 6, 7 and 8, wherein the napkin 30 also includes a base layer 31 of absorbent sheet material, a cover layer 32 of absorbent sheet material, a wrapping layer 33, elongate absorbent pads 34 and 35 and an elongate sponge 37 of flat, rectangular cross-sectional shape. The base layer 31, cover layer 32 and wrapping layer 33 are substantially identical to the corresponding base layer, cover layer and wrapping layer of FIGS. 1-5. The sponge 37 is made of the same compressed sponge material as described for FIGS. 1-5, but is flat and includes indentations or score marks, with the indentation 36 extending along the length of the sponge and with the indentations 38 extending across the length of the sponge. The sponge 37 is relatively stiff when dry and compressed. The indentations 38 tend to cause the dry sponge to be more bendable along its length, thereby permitting the napkin 30 to freely bend without restraint from the sponge 37. The longitudinal score 36 tends to control the shape of the sponge when the sponge has become swollen by contacting and absorbing menstrual fluids. As illustrated in FIG. 8, the longitudinal score 36 tends to form a longitudinal recess in the sponge when the sponge has absorbed a liquid and has become swollen.

As with the first embodiment illustrated in FIGS. 4 and 5, the sponge 37 of the embodiment illustrated in FIGS. 7 and 8 is of relatively short profile when dry, but when the sponge swells it increases in profile, becomes very soft and tends to fill the spaces available within the napkin.

As illustrated in FIGS. 9, 10 and 11, a third embodiment of the napkin 40 is illustrated and includes a base layer of absorbent sheet material 41, a cover layer 42 of absorbent sheet material, a wrapping layer 43, elongate absorbent pads 44 and 45 and an elongate sponge 47. This embodiment of the napkin is similar to the embodiment of FIGS. 6–9 but sponge 47 is circular in cross-section. The sponge 47 is scored or indented at 46 at intervals along its length so as to enhance its bendability. Sponge 47 is positioned over the adjacent surfaces of the pads 44 and 45, and when the sponge is contacted by menstrual fluids and begins to swell, it tends to fill the spaces between the pads 44 and 45 and the other spaces available within the confines of the napkin, as illustrated in FIG. 11.

As illustrated in FIGS. 12, 13 and 14, a fourth embodiment of the napkin 50 is disclosed and includes the base layer 51 of absorbent sheet material, the cover layer 52 of absorbent sheet material, the wrapping layer 53 of substantially liquid-impervious sheet material, and an elongate sponge 57. In this embodiment of the invention no additional elongate absorbent pads of the type shown in FIGS. 1–11 are utilized, and sponge 57 is of circular cross-section and is located between the base layer and cover layer. When the sponge 57 is contacted by menstrual fluids, it tends to expand and to occupy the space available between the base layer and cover layer, as illustrated. Sponge 57 is also scored or indented at spaced intervals along its length, as illustrated at 56 in FIG. 12, so as to enhance the bendability of the sponge, and therefore not restrain the bendability of the napkin.

FIGS. 15, 16 and 17 show yet another embodiment of the napkin 60 and includes a base layer 61 of absorbent sheet material, a cover layer 62, a wrapping layer 63 and an elongate sponge 67. The sponge 67 is semicircular in cross-section with its flat surface 66 facing the base layer 61 of sheet material and with its curved surface 68 facing the cover layer 62. When the sponge 67 swells, it tends to expand between the base layer 61 and cover layer 62, causing the cover layer to protrude slightly away from the base layer. The sponge 67 is indented or scored at intervals along its length, as indicated at 66 in FIG. 15. This enhances the bendability of the sponge and therefore the sponge does not tend to retard the bendability of the napkin.

As illustrated in FIGS. 18, 19 and 20, another embodiment of the napkin 70 is disclosed which comprises a base layer 71, a cover layer 72, a wrapping layer 73 and an elongate sponge 77 between the base layer 71 and wrapping layer 72. The sponge 77 is a flat sheet and is of approximately rectangular cross-sectional shape. The sponge 77 is scored or indented at intervals extending across its length as illustrated at 76. This enhances the bendability of the sponge when in its dried state, and therefore does not retard the bendability of the napkin. When the sponge swells as illustrated in FIG. 20, the sponge tends to expand between the base layer 71 and cover layer 72 to cause a slight protrusion extending longitudinally of the napkin.

Double-face adhesive strip material can be applied to the outer surface of the wrapping layer of each embodiment as indicated at 78 of FIGS. 19 and 20 for the purpose of attaching the napkin to the undergarment of the wearer.

It will be noted that in all of the embodiments of the invention the sponge is located centrally of the napkin, and in most embodiments the sponge is located in a position where it is likely to be contacted by the menstrual fluids emitted from the wearer. Moreover, it will be noted that the cross-sectional area of the napkin is smaller before the sponge has been contacted by menstrual fluids, so that the napkin is less bulky and is likely to be more comfortable to the wearer when first placed in position, and when the fluids contact the napkin, the napkin tends to grow in cross-sectional area, tends to become softer, and tends to grow in a manner that conforms to the shape of the anatomy of the wearer, therby minimizing any discomfort to the wearer.

While this invention has been described in detail with particular reference to a preferred embodiment thereof, it will be understood that variations and modifications can be effected within the spirit and scope of the invention as described hereinbefore and as defined in the appended claims.

We claim:

1. A sanitary napkin comprising a plurality of elongate absorbent pads arranged parallel to one another and in a bundle generally triangular in cross-section with a first layer of pads arranged in side-by-side relationship, a pad overlying the pads of the first layer of pads at a position over the adjacent surfaces of the pads in the first layer and forming a second layer of pad material, an elongated swellable sponge positioned between said first layer of pads and said second layer of pad material, a liquid-pervious material surrounding all of said pads for holding the pads in an uncompressed bundled relationship with the pads movable longitudinally with respect to one another, a sheet of liquid-impervious material substantially covering the bottom portion of the first layer of pads, and a layer of adhesive material disposed on the bottom portion of said napkin for securing said napkin to an undergarment, as a result of the napkin not being compressed said napkin being characterized by being bendable along its length with portions of some of the pads movable longitudinally with respect to others of the pads as the napkin is bent along its length whereby the napkin is placed in external contact with the female human body with the second layer of pad material in aligned contact with the labia and with the first layer of pads holding the second layer of pad material in contact with the labia and bending the napkin along its length as necessary to conform to the curvature of the external surfaces of the anatomy adjacent the labia.

2. The sanitary napkin of claim 1 and wherein each of said absorbent pads are approximately of circular shape across their lengths.

3. The sanitary napkin of claim 1 and wherein the ends of some of the pads at the ends of the napkin are staggered with respect to each other.

4. A sanitary napkin comprising a plurality of elongate absorbent pads arranged parallel to one another in an elongated uncompressed bundle, at least one of said pads being positioned centrally in said bundle and characterized by having been formed of compressed swellable sponge material, and a wrapper of a liquid-pervious material surrounding all of said pads and closed at its ends about said pads for maintaining the pads in a bundle, and as a result of the napkin not being compressed portions of said pads are movable with respect to one another along the lengths of the pads and the napkin is bendable along its length when placed in external contact with the female human body with the centrally positioned pad of sponge material aligned with and placed adjacent the labia and with the napkin curved along its length as necessary to conform to the curvature of the external surfaces of the anatomy, and when the sponge is contacted with menstral fluids issued from the wearer the sponge tends to become softer and tends to swell into a shape that conforms to the anatomy of the wearer.

5. The sanitary napkin of claim 4 and wherein the pad of sponge material is dry and scored across its length at intervals along its length whereby the pad of sponge material is bendable along its length.

6. A sanitary napkin comprising a pair of elongate absorbent pads arranged in side-by-side relationship, an elongate compressed swellable sponge extending along the adjacent surfaces of the absorbent pads, a wrapper of liquid-pervious material surrounding said pads and sponge for maintaining said pads and sponge in a bundle, said sponge being supported by said absorbent pads and forming a ridge extending along the napkin, said pads and said sponge being movable with respect to one another along their lengths and the napkin being bendable along its length when placed in external contact with the human body with the sponge aligned with and placed adjacent the labia and with the pads holding the sponge adjacent the labia and the napkin curved along its length as necessary to conform to the curvature of the external surfaces of the the anatomy, whereby, when menstral fluids of the wearer contact the sponge, the sponge becomes softer and tends to swell to a shape that conforms to the anatomy of the wearer.

7. The sanitary napkin of claim 6 and wherein said sponge is shaped at itervals along its length to enhance its bendability along its length.

8. The sanitary napkin of claim 6 and wherein said sponge is a bio-compatible, polymeric, elastomeric, lint-free, uniformly swellable hydrophilic sponge.

9. The sanitary napkin of claim 6 and wherein said sponge is approximately circular in cross-section.

10. The sanitary napkin of claim 6 and wherein said sponge is approximately rectangular in cross-section.

11. The sanitary napkin of claim 6 and wherein said sponge is approximately semi-circular in cross-section.

12. A sanitary napkin comprising an elongated generally flat base layer of absorbent sheet material, an elongate dry swellable sponge extending along and protruding away from said base layer of sheet material and supported by said base layer of sheet material, a cover layer of absorbent sheet material joined at its edge portions to the edge portions of said base layer of sheet material and covering said sponge, said sponge being narrower than the base layer of sheet material and forming in the napkin an elongate ridge that protrudes from the base layer, said sponge being bio-compatible, polymeric, elastomeric, lint-free and uniformly swellable, and characterized by an absorption capacity for liquids in excess of twenty times the weight of the sponge, whereby when the napkin is placed with the sponge adjacent the labia of the wearer the sponge tends to fit the anatomy of the wearer and when the sponge is contacted with menstrual fluids issued from the wearer it tends to become softer and to swell to a shape that conforms to the shape of the anatomy of the wearer.

13. The sanitary napkin of claim 12 and wherein said sponge is substantially semicircular in cross-section and is shaped across its length at intervals along its length to enhance its bendability.

14. The sanitary napkin of claim 12 and wherein said sponge is substantially circular in cross-section and is shaped across its length at intervals along its length to enhance its bendability.

15. The sanitary napkin of claim 12 and wherein said sponge is scored across its length to enhance its bendability.

16. A sanitary napkin comprising at least three elongate absorbent pads arranged parallel to one another in an elongated uncompressed triangular bundle, a first layer of said pads comprising two pads arranged in side-by-side relationship and the third pad positioned in a second layer overlying the adjacent surfaces of the pads in the first layer of pads, the pad in the second layer of pads being characterized by having been formed of compressed swellable sponge material, and a wrapper of a liquid-pervious material surrounding all of said pads and closed at its ends about said pads for maintaining the pads in a bundle, and as a result of the napkin not being compressed portions of said pads are movable with respect to one another along the lengths of the pads and the napkin is bendable along its length when placed in external contact with the female human body with the pad in the second layer of pads aligned with and placed adjacent the labia and with the other pads holding the one pad adjacent the labia and with the napkin curved along its length as necessary to conform to the curvature of the external surfaces of the anatomy.

* * * * *